United States Patent [19]

Coustre et al.

[11] 4,374,424
[45] Feb. 15, 1983

[54] APPARATUS AND METHOD FOR PLOTTING A CHROMATOGRAM

[75] Inventors: André Coustre; Robert Elitzsch; Jean-Claude Caullier, all of Conflans-Sainte-Honorine, France

[73] Assignee: Delsi, Suresnes, France

[21] Appl. No.: 96,669

[22] Filed: Nov. 23, 1979

[30] Foreign Application Priority Data

Nov. 28, 1978 [FR] France ............... 78 33607

[51] Int. Cl.³ ............................................ G01N 31/08
[52] U.S. Cl. ................................. 364/497; 73/23.1; 364/900
[58] Field of Search ............... 364/497, 573, 900, 571, 364/498, 577; 73/23.1

[56] References Cited

U.S. PATENT DOCUMENTS

| | | | |
|---|---|---|---|
| 3,562,501 | 2/1971 | Mears | 73/23.1 |
| 3,614,408 | 10/1971 | Watkin et al. | 364/497 |
| 3,797,300 | 3/1974 | Sato | 73/23.1 |
| 3,898,837 | 8/1975 | Boege | 73/23.1 |
| 4,063,310 | 12/1977 | McDonald | 364/900 |
| 4,180,857 | 12/1979 | Yoshihara et al. | 364/497 |
| 4,229,968 | 10/1980 | Muldoon | 364/497 |

OTHER PUBLICATIONS

Briggs; "Computer-Controlled Chromatographs", Control Engineering; vol. 14, No. 9; Sep. 1967, pp. 75-80.

Primary Examiner—Errol A. Krass
Attorney, Agent, or Firm—Cushman, Darby & Cushman

[57] ABSTRACT

An apparatus and method for digitally displaying with a thermal printer the continuous time varying signal generated by a chromatograph. The apparatus generates different graphic forms distinguishing chromatograph peaks representing a solvent from the chromatograph peaks indicative of compounds dissolved in the solvent. The continuous chromatograph signal is sampled at predetermined intervals at the onset of a peak. These sample values are stored in a memory that is sequentially addressed with one address corresponding to each sample. From the samples taken, individual bits of baseline data are calculated and stored in memory having addresses corresponding to those wherein their respective corresponding sample values are stored. Instructions for printing different graphic patterns are also stored and called-up to print a display indicative of the sample values and corresponding base-line information so that a reader can easily distinguish the peaks and baseline. The arrangement is particularly well suited for driving a thermal printer.

7 Claims, 8 Drawing Figures

APPARATUS AND METHOD FOR PLOTTING A CHROMATOGRAM

The invention relates to an apparatus and method for digitally plotting a chromatogram and the results of integration of the peaks.

A chromatograph analyzes a chemical mixture to determine its constituent parts. These constituent parts are represented by a continuous time varying signal having peaks and valleys.

In addition to the locations of the peaks and valleys the areas of the curves associated with the peaks and valleys are meaningful to those in the chromatograph art. It is desirable to be able to inexpensively display chromatograph information in an easy to read yet meaningful manner. Known arrangements for displaying chromatograms include automatically plotting the analog signal representing the chromatograph signal without a baseline, separately calculating baseline data from the analog curve and then manually adding the baseline data to the automatically plotted chromatogram curve or printing the baseline data. The present invention provides an arrangement for automatically displaying the chromatogram curve with baseline information. This is accomplished by providing a control system for manipulating the chromatogram data and generating signals for driving a relatively inexpensive thermal printer. FIG. 1a shows the head of a thermal printer 1 in an upturned position in relation to its working position so as to show the p pinpoint heating elements 2 which it comprises. Elements 2 are aligned parallel to the direction of movement of the recording paper indicated by arrow 3, whereas printer head 1 moves from left to right while occupying successively N positions evenly distributed over the width of the recording so as to print dots placed on p consecutive lines. To each position of the printer head there corresponds a character of p bits, stored in the memory at the address corresponding to this position. In this character each bit having a value "1" causes the printing of a dot, whereas the value "0" causes a blank (no printing of a dot). FIG. 1a shows at 4 a grid having p lines and N columns, only the points of intersection of which are printed, as is the case for example for the series of dots 5 belonging to curve portion 6 and for the series of dots 7 belonging to curve portion 8. After reaching the right-hand edge of the recording, the printer head returns and stops at the left-hand edge while the paper advances p lines. All is ready for a new scanning to begin. FIG. 1b shows the block diagram of the control unit of the printer. This unit comprises a microprocessor 12 and various peripheral units as follows:

read-only memory 13;
main memory 14;
duration controller 15;
interface gates 16 to 21;
an address gate 22 and an address decoder 23;
an interruption controller 24;
an address and data bus 25.

Gate 16 receives in digital form, from a known chromatogram apparatus, the ordinates of the current dot, i.e. the magnitude of the analog signal, of the chromatogram during successive sampling intervals. It also receives peak begin and end signals for identifying the starting and stopping points of a peak of the chromatogram signal, as well as the signals indicating the presence of a valley and, after plotting the end of the peak of the chromatogram, the results of integration of the peaks, i.e. the area of the curve under the peak.

Gate 17 is assigned to receive instructions such as the speed of travel of the paper of the printer, order to plot the baseline, discontinuance of the preceding order.

Gate 18 forms a preadjusted attenuator. Gates 16, 17 and 18 are connected by terminals 26 to 28 to the integrator of the chromatograph and by their outputs to the address and data bus 25.

Gate 19 is connected by its inputs to the printer and by its outputs to bus 25. It allows the microprocessor to control the execution of the plot.

Gate 20 is connected by its inputs to bus 25 and by its outputs to the printer. It allows microprocessor 12 to provide signals for controlling the movement of the printing head.

Gate 21 is connected to bus 25 by its inputs and to the heating elements of the printing head by its outputs.

The control unit thus formed is capable of elaborating the printing instructions for each peak and its numerical reference. Moreover, after plotting of the chromatogram, this unit causes the printing of a table of the results of integration of the peaks and their numerical reference to be initiated.

The object of the present invention is to utilize a printer of the type which has just been described and its control unit so as to carry out printing of a first type between the curve of the solvent and its baseline and printing of a second type between the peak of each compound in solution and the limits which correspond thereto.

The present invention provides a process of graphical representation of chromatograms from information supplied by an integrator-computer in which instructions for printing the chromatographic signal are successively entered into a main memory at an address corresponding to the moment of sampling the instructions defining the sample value. The reception of the end-of-peak signal causes the elaboration of the instructions for printing the baseline successively to the sample values from information delivered by the chromatograph integrator. Each baseline instruction is entered into a cell of the memory at an address corresponding to the movement of sampling and on the elaborated value according to the invention. The cells of the main memory corresponding to said moment of sampling are then scanned, from the one which contains the instructions for printing the elongation to the one which contains the instructions for printing the baseline, in synchronism with those having the same address in an additional read-only memory containing the instructions for printing the graphic form in that said instructions are transferred into the cells of said main memory. The areas of the peaks are filled in with graphic forms which differentiate them from the recording medium.

The preferred embodiment of the apparatus of the present invention for implementing the process includes at least one additional read-only memory containing the instructions for printing the graphic form to be represented on the area of the peaks comprising lines and a number of addresses in the line equal to the number of dots contained in the width of the recording.

The invention has the following advantages:

it is possible to improve the device for implementing the prior process with a view to adapting it to the new process for a small extra cost;

the duration of the plotting of a chromatogram is not substantially modified because the additional operations relative to each peak may be carried out during the wait for numerical data concerning the following peak;

the new possibility provided is added to the preceding one without excluding any of them.

The invention will be better understood by referring to the description which follows accompanied by FIGS. 2 to 7 given by way of non-limiting illustration, in which:

FIG. 2 shows the sequence of operations concerning the plotting of a peak by the process according to the invention. Operations 30 to 38 are reproduced for eack peak that the chromatograph treats in an independent manner:

Figure 3:
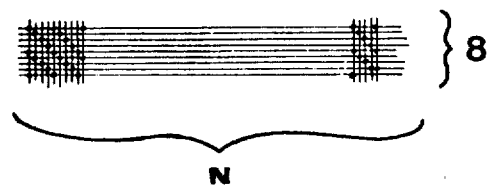
FIG. 3 shows a graphic form contained in the additional read-only memory.

30 shows the entry into the main memory of the peak begin signal delivered by the integrator of the chromatograph. This signal includes the rank order of the sampling interval and the elongation of the chromatogram in this interval;

31 shows the entry into the main memory of the instructions for printing the current dot of the peak in a cell whose address depends on the rank order of the sampling interval and the elongation of the current dot;

32 shows, when it exists, the entry into the main memory of the instructions for printing a valley signal between two non-separated peaks. This signal is written into a cell whose address depends on the rank order of the sampling interval during which occurs the signal for the valley and for the elongation of the chromatogram at the low point of the valley;

33 shows the entry of the instructions for printing the end-of-peak signal in the cell of the address memory resulting from the rank order of the interval during which this signal and the elongation of the chromatogram at the moment of the end of the peak occurred;

34 shows the elaboration of the baseline of the peak by interpolation in each interval between the peak begin and end signals;

35 shows the entry of the instructions for printing the dot of the baseline in the address cell resulting from the rank order of the interval and the value obtained by interpolation;

36 shows the simultaneous scanning of the cells of the main memory, between the cell containing the dot of the peak and that containing the dot of the baseline, and cells of an additional read-only memory containing the graphic form to be reproduced. The scanning of the additional memory begins at the first line and advances a line at each new sampling interval until the last line with return to the first line as many times as is required. The number of lines which the additional memory comprises is a multiple of eight and each line is formed from a number of N cells equal to the number of positions which the printing head can occupy during one scanning. The graphic form to be reproduced on the area of the peak is stored in the additional memory by causing the binary states "1" to correspond to the dots and the "0" to the blanks. When the printing to be reproduced is as simple as hatching, eight lines are sufficient, as is shown in FIG. 3. Simultaneous scanning of the cells of the two memories is effected by causing the addresses in the line to correspond and it is accompanied by putting the cells of the main memory to state "1" corresponding one by one to the cells of the read-only memory in state "1".

Operations 34, 35 and 36 are repeated as often as is necessary to reach the peak end signal.

37 shows the entry into the main memory of the printing instructions corresponding to the valley signal stored in an extension of the read-only memory. The graphic form will comprise in this case for example a white straight line segment between two peaks or else a black straight line segment.

38 shows the delivery of a printing order each time that the number of lines of the main memory having received the instructions for printing the graphic form is equal to that of the elements of the printing head.

Figure 4:
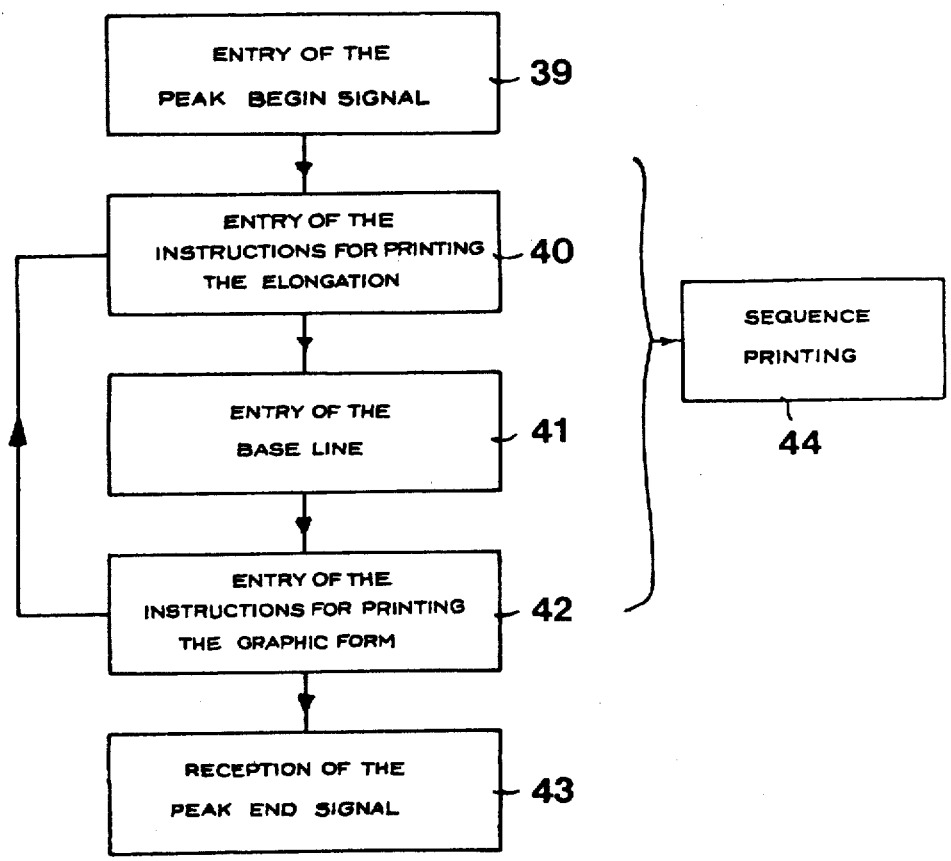
FIG. 4 shows the sequence of operations of the process of the invention concerning the plotting of the peak of the solvent.

FIG. 4 shows the succession of the operations concerning the plotting of the peak of the solvent from signals from the integrator of the chromatograph:

39 shows the entry into the main memory of the peak begin signal. This signal includes the rank order of the interval and the elongation of the chromatogram in this interval.

40 shows the entry into the memory of the instructions for printing the current dot of the peak.

41 shows the entry into the main memory of the instructions for printing a dot having the same elongation as the peak begin signal. This dot forms part of the baseline of the peak of the solvent.

42 is the scanning of a second additional memory containing the graphic form to be reproduced in the area of the peak of the solvent effected in a similar way to what has already been said in connection with operation 36 and the putting of the cells of the main memory to state "1" corresponding one by one to the cells of the read-only memory in state "1". The repetition of operations 40, 41 and 42 continues as often as is necessary to reach the end of the peak. This is shown by the arrow going from the end of operation 42 to operation 40.

43 shows the entry of the instructions for printing the end signal of the peak of the solvent in the main memory.

44 shows a printing sequence which occurs each time that the number of lines of the main memory having received the instructions for printing the graphic form is equal to that of the elements of the printing head.

Figure 2:
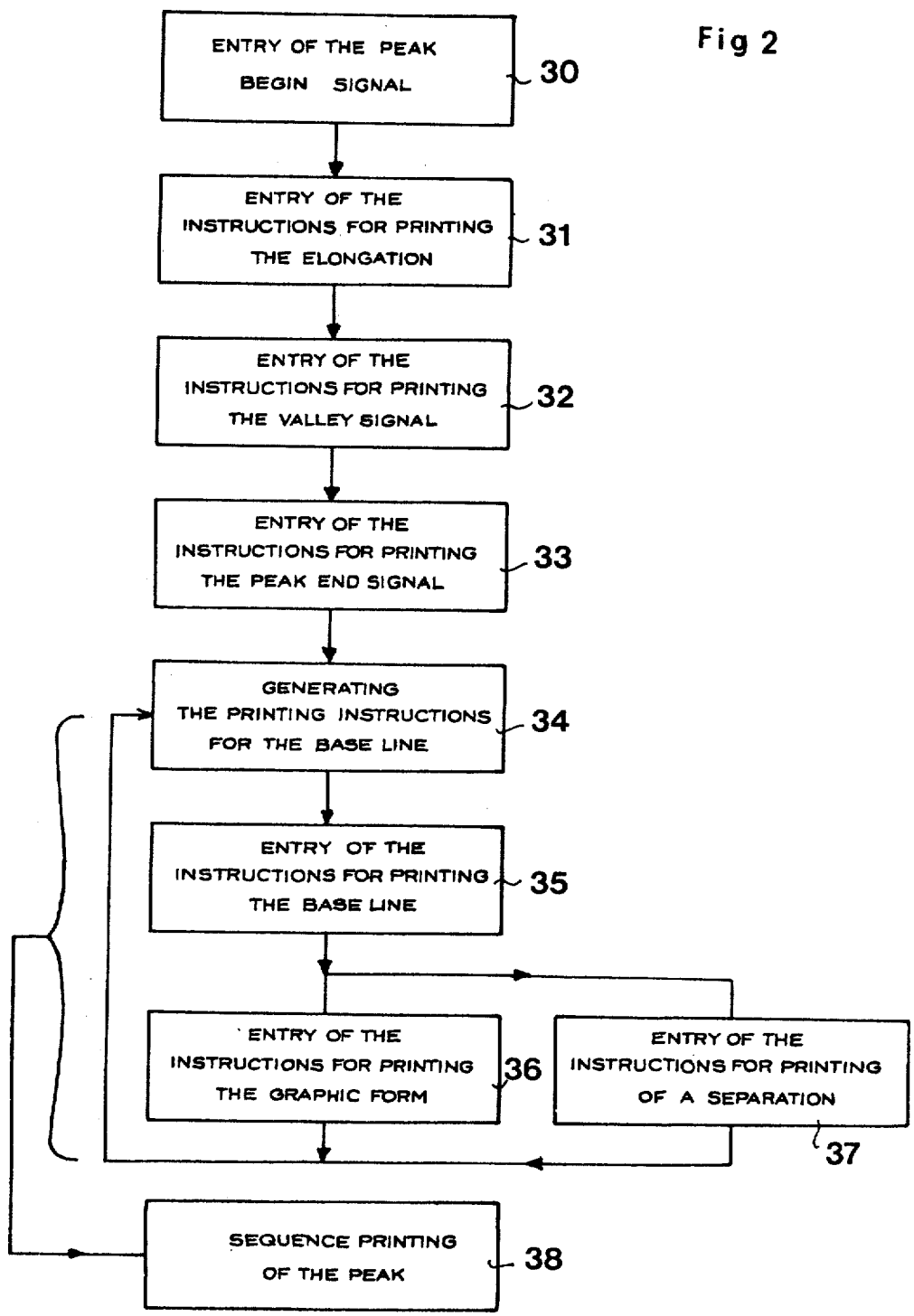
FIG. 2 shows the sequence of operation of the process of the invention concerning the plotting of a peak of a compound in solution.
Figure 5:
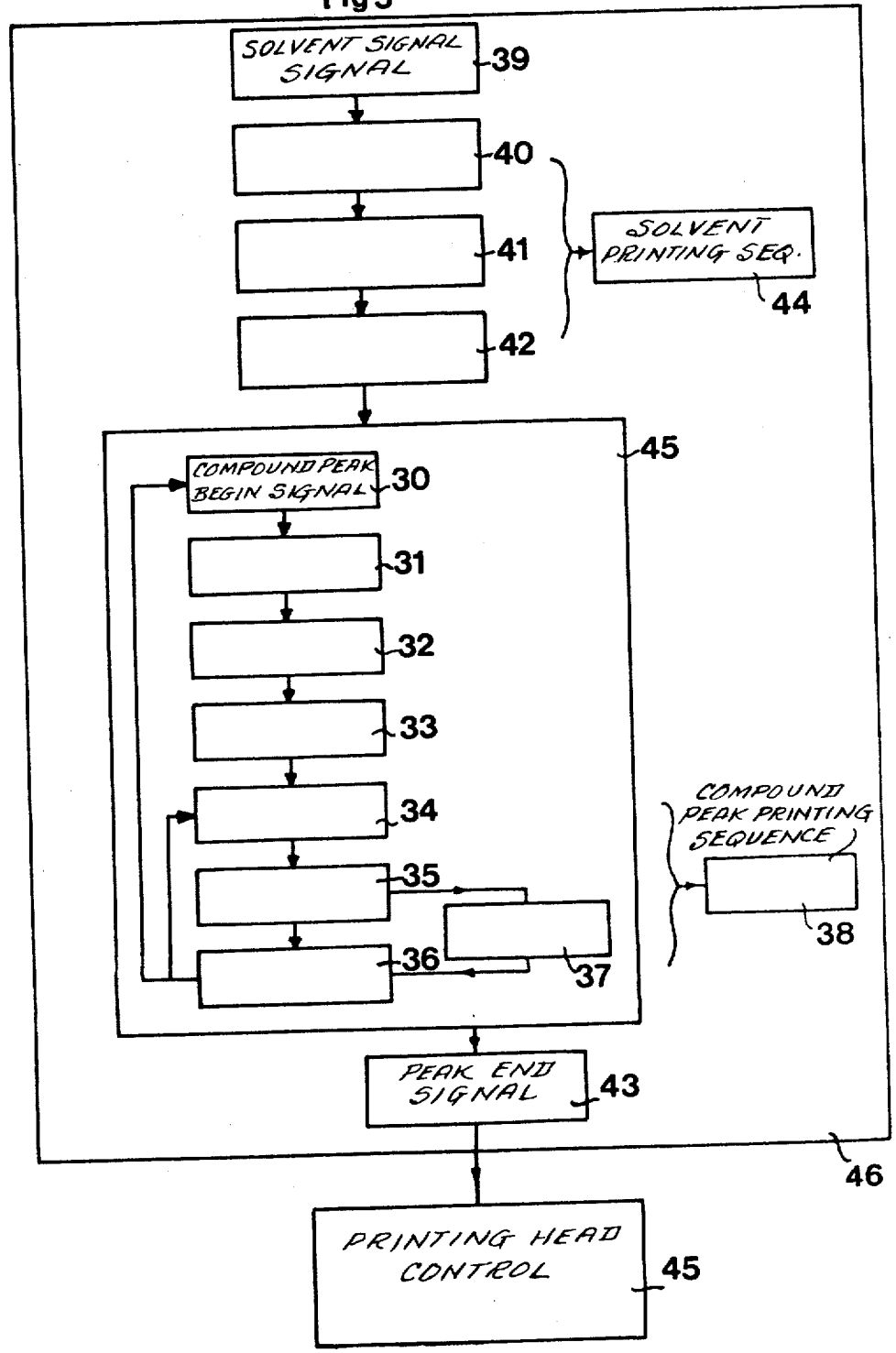
FIG. 5 shows the plotting of a peak during the end of the peak of the solvent.

FIG. 5 shows the succession of operations concerning the plotting of a chromatogram comprising peaks due to the dissolved chemical compound located during the end of the peak of the solvent. Frames 45 represent the operations described in connection with FIG. 2. The arrow containing the end of operation 36 to the beginning of operation 30 recalls that the cycle begins again at each dissolved compound peak. The arrow connecting the end of operation 36 to the beginning of operation 34 recalls that the main memory is filled interval by interval, a first graphic form being used between the peak of a dissolved compound and its baseline and a second graphic form being used between said baseline of the dissolved compound and that of the peak of the solvent. Frame 46 contains all the operations occurring during the peak of the solvent in particular. The printing sequences 44 which occur before the appearance of the dissolved compound peaks are produced during the advance of the chromatogram. The printing orders 38 are only given after the peak end signal of a dissolved compound when the number of processed lines of the main memory is equal to the number of the elements of the printing head.

Figure 1A:
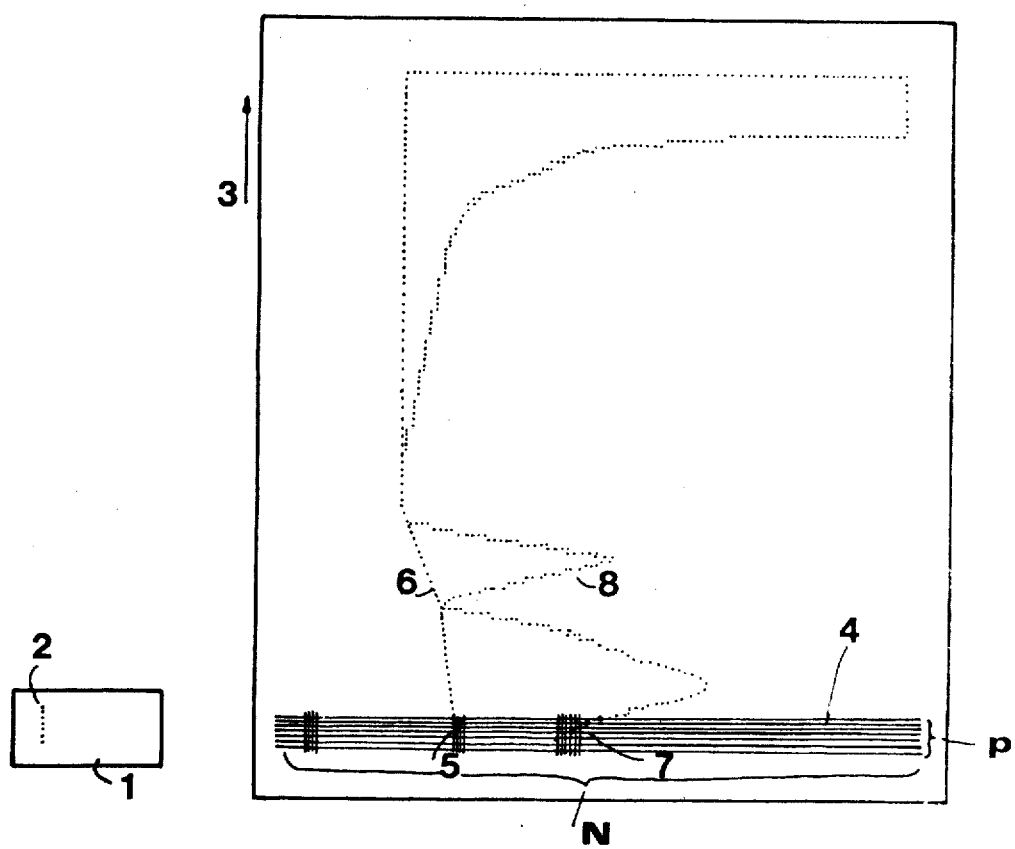
Figure 1B:
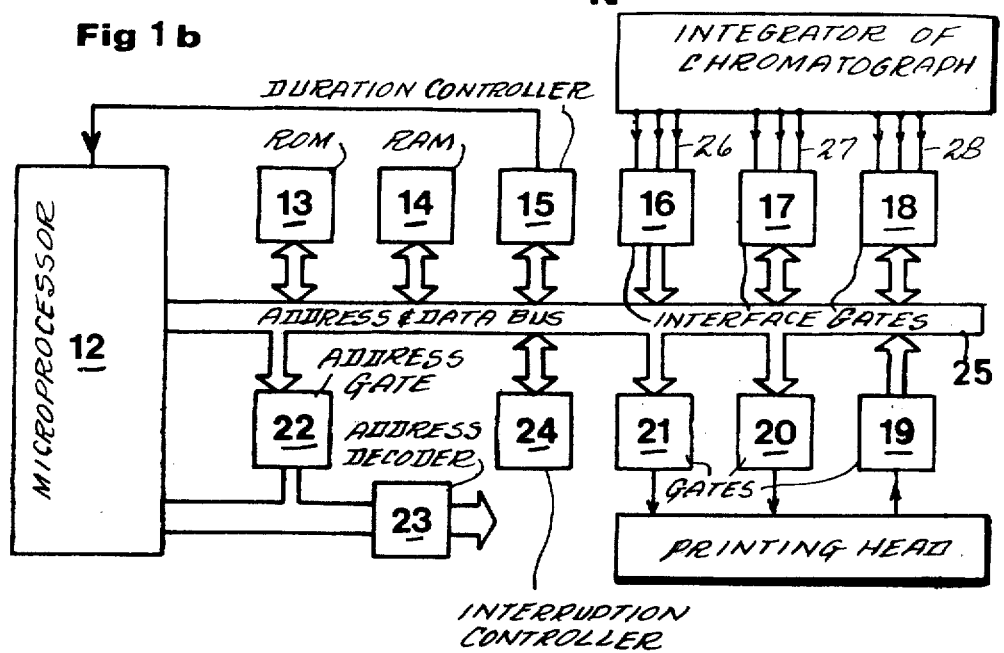
Figure 6:
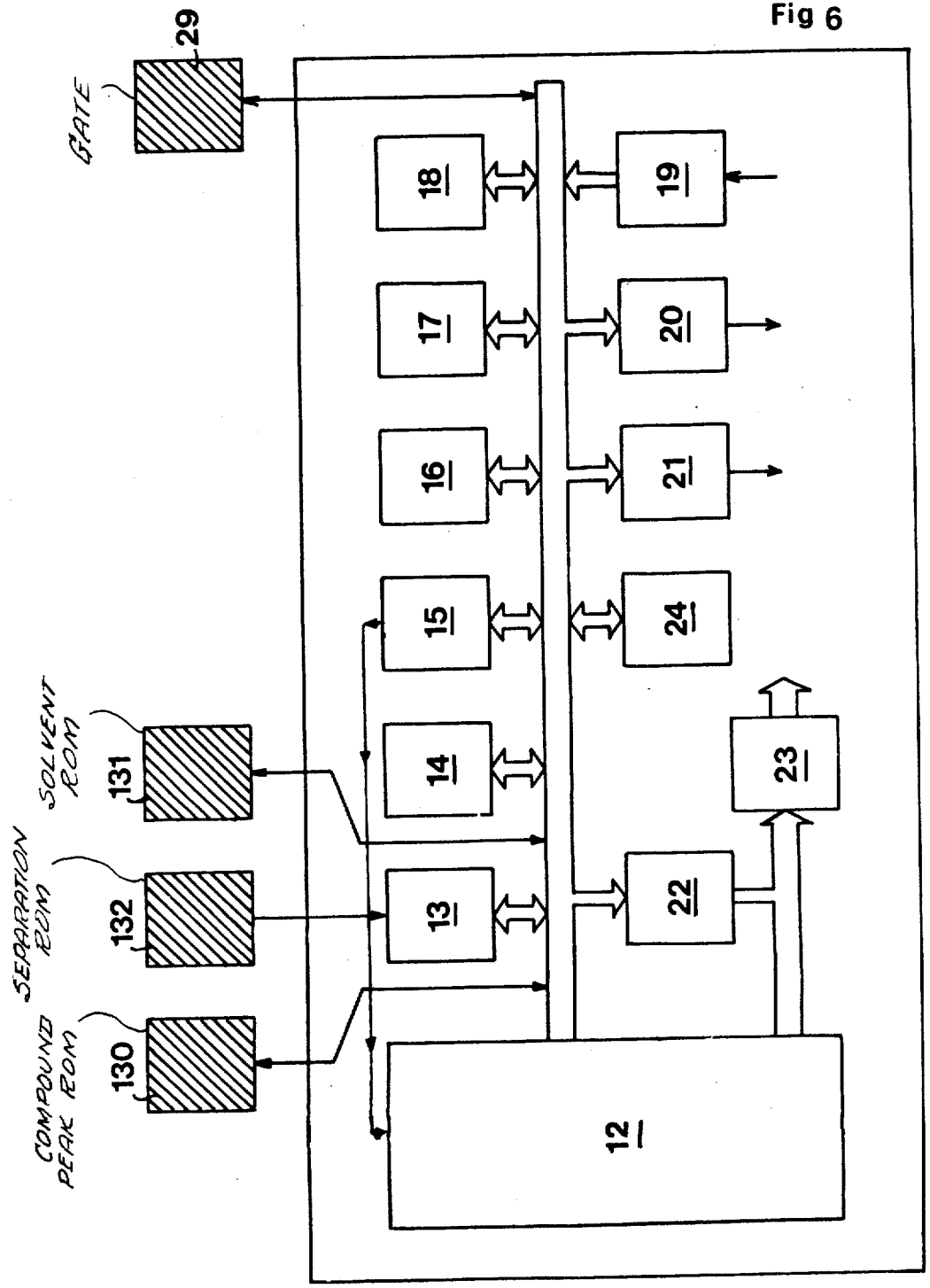
FIG. 6 shows the block diagram of the device for implementing the process of the invention.

FIG. 6 shows the block diagram of the device for implementing the process of the invention. In this figure, the elements already met in connection with FIG. 1b have kept the same numerical reference and are shown by plain cells. The additional elements are shown by hatched cells. In this figure:

130 is a first additional read-only memory containing in binary form the graphic form for representing the compounds in solution, the cells in binary state "1" corresponding to a printed dot and the cells in binary state "0" corresponding to a blank on the chromatogram.

131 is a second additional read-only memory containing the graphic form for representing the solvent. The cells in binary state "1" correspond to the dots printed on the chromatogram and the cells in binary state "0" correspond to a blank.

132 is a complement to memory 13 containing the instructions relative to the between-peak separations.

29 is an additional interface gate for discontinuing the printing on the area of the peaks.

By way of example, the Applicant has constructed the device for implementing the process which has just been described by means of the following elements commercialized by the American firm INTEL at Santa Clara:

1 microprocessor 8085;
2 read-only memories 2716;
3 additional read-only memories 2716;
6 main memories 2114;
1 duration controller 8253;
1 interruption controller 8259;
1 address decoder 8205;
9 interface gates 8212;
2 eight-conductor buses;

as well as a printer T80 commercialized by Data Products 6219 De Soto Avenue at Woodland Hills, in Ca., in which the number p of heating elements is equal to 7 and the number N of dots per line is equal to 560.

The printing contained in the first additional read-only memory is formed by vertical hatchings reproduced every seven sampling intervals.

The printing contained in the second read-only memory is formed by horizontal hatchings.

The vertical separations between adjacent peaks are formed by a black line going from the baseline to the lowest dot of the valley between the peaks.

Figure 7:
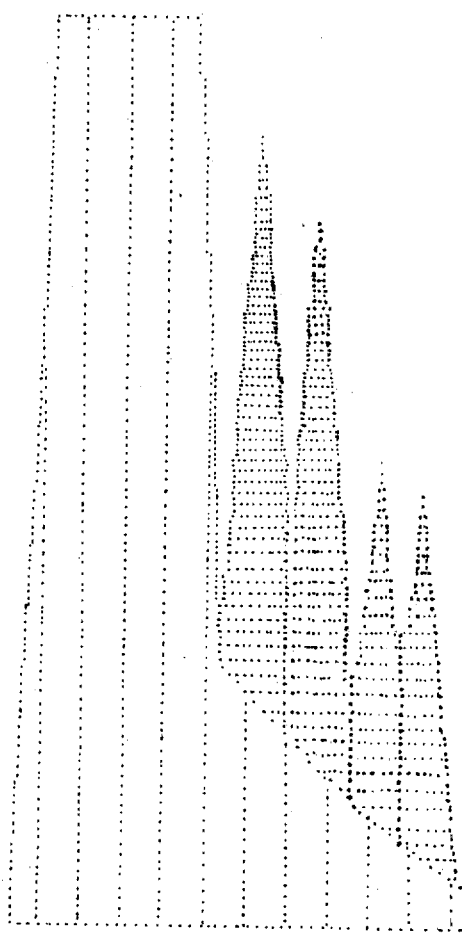
FIG. 7 shows the plotting of a chromatogram effected by means of the device for implementing the process of the invention.

FIG. 7 is a partial view of a chromatogram plotted by means of the implementing device of the invention.

We claim:

1. A method for displaying a continuous signal having a time varying elongation and including at least one peak provided by an external analysis apparatus, comprising the steps of:
sampling the continuous signal at a plurality of sampling times and determining an elongation value of the continuous signal for each sample;
detecting the starting time and ending time for the peak of the continuous signal;
storing the elongation values for each sample taken from the starting time to the ending time of the peak;
calculating, from the elongation values, baseline data comprising baseline magnitude values corresponding to the sampling times and varying from a baseline value corresponding to the elongation value at the starting time of the peak to a baseline value corresponding to the elongation value at the ending time of the peak; and
generating a printing control signal from the stored data and the calculated baseline data for commanding an external printer to print the elongation values and corresponding baseline data in the form of a graphic.

2. A method according to claim 1 wherein the generating step comprises the step of generating a plurality of dots for each elongation value and corresponding baseline value, the plurality of dots being printed between the elongation value and corresponding baseline value.

3. A method according to claim 1 further comprising the step of calculating, from the stored data, an area defined by each peak and its corresponding baseline.

4. A method according to claim 1 wherein the continuous signal represents a chromatogram.

5. A method according to claim 1 further comprising the step of detecting a valley point of the continuous signal and wherein the generating step includes the step of generating a control signal commanding the printing of dots corresponding to the sampling time of the valley point and elongation values varying from the stored elongation value at the valley point sampling time to the calculated baseline elongation value at the valley point sampling time.

6. A display apparatus for displaying a continuous signal having a time-varying elongation and including at least one peak provided by an external analysis apparatus, comprising:
means for sampling the continuous signal at predetermined sampling times;
means for generating a digital signal indicative of the elongation value of each sample;
means for detecting the starting time and ending time for the peak;
means for generating by interpolation baseline data corresponding to the sampling times from the start to the end of the peak;
memory means for storing (a) the elongation values of samples taken from the start to the end of the peak and (b) the baseline data, the elongation values and baseline data being stored at sequentially addressed locations within the memory means corresponding to the sequential sampling times;
means for generating a printing control signal indicative of the stored elongation values and baseline data;
means for initiating the operation of the generating means at the ending time of the peak;
a printer having a printing head; and
means, responsive to the printing control signal for causing the printing head to print the elongation values and corresponding baseline data in the form of a graphic.

7. A display apparatus according to claim 6 wherein the continuous signal is supplied by a chromatograph analyzing compounds dissolved in a solvent and wherein the apparatus further includes:
a first additional memory for storing a first graphic pattern to be printed representing a solvent peak; and
a second additional memory for storing a second graphic pattern to be printed representing a compound peak.

* * * * *